(12) United States Patent
Sanders et al.

(10) Patent No.: US 8,348,952 B2
(45) Date of Patent: Jan. 8, 2013

(54) SYSTEM AND METHOD FOR COOLING A SPINAL CORRECTION DEVICE COMPRISING A SHAPE MEMORY MATERIAL FOR CORRECTIVE SPINAL SURGERY

(75) Inventors: Marc M. Sanders, North Yorkshire (GB); Thomas Allard Xander Bonnema, Hengelo (NL); Kevin Michael Amesbury, Derbyshire (GB); Paul John Firkins, Worcs (GB)

(73) Assignee: DePuy International Ltd. (GB)

( * ) Notice: Subject to any disclaimer, the term of this patent is extended or adjusted under 35 U.S.C. 154(b) by 979 days.

(21) Appl. No.: 11/340,259

(22) Filed: Jan. 26, 2006

(65) Prior Publication Data

US 2007/0191831 A1     Aug. 16, 2007

(51) Int. Cl.
  *A61F 2/46*     (2006.01)
  *A61F 2/44*     (2006.01)
  *A61B 17/88*    (2006.01)
(52) U.S. Cl. ..... 606/86 R; 606/279; 606/246; 623/17.11
(58) Field of Classification Search .................. 606/80, 606/102, 86 A, 86 B, 86 R, 279, 246–247, 606/251–257, 261–262; 623/17.11–17.16
See application file for complete search history.

(56) References Cited

U.S. PATENT DOCUMENTS

| | | |
|---|---|---|
| 2,669,896 A | 2/1954 | Clough |
| 2,952,285 A | 9/1960 | Roosli |
| 3,604,487 A | 9/1971 | Gilbert |
| 3,786,806 A | 1/1974 | Johnson et al. |
| 3,915,160 A | 10/1975 | Lode et al. |
| 4,289,123 A | 9/1981 | Dunn |
| 4,363,250 A | 12/1982 | Suga |
| 4,592,933 A | 6/1986 | Meyerson et al. |
| 4,611,582 A | 9/1986 | Duff |
| 4,697,582 A | 10/1987 | William |
| 4,733,657 A | 3/1988 | Kluger |
| 4,743,260 A | 5/1988 | Burton |

(Continued)

FOREIGN PATENT DOCUMENTS

DE     3923996 A1    1/1991

(Continued)

OTHER PUBLICATIONS

Advanced Energy, Industrial Processes: "Infrared (IR) Heating," "Microwave Heating," "Radio Frequency" and "Catalytic Heating," (2003).

(Continued)

*Primary Examiner* — Thomas Barrett
*Assistant Examiner* — Matthew Lawson
(74) *Attorney, Agent, or Firm* — Nelson Mullins Riley & Scarborough LLP (57) ABSTRACT

A device and method of correcting a spinal defect in a patient employs the use of shape memory material in a spinal correction device. The shape memory material may be transitioned between a flexible martensitic state to allow shaping of the spinal correction device and a rigid austenitic state to apply corrective forces to the spine. The shape memory material may be transitioned to the flexible martensitic by applying a coolant, such as cold gas, directly or indirectly to the shape memory material to transfer heat away from the material. The cooling device and method may allow for in-vivo shaping of the spinal correction device while inserted in the body and attached to bone anchors by cooling the spinal correction device after insertion.

23 Claims, 7 Drawing Sheets

U.S. PATENT DOCUMENTS

| | | | |
|---|---|---|---|
| 4,887,596 A | 12/1989 | Sherman | |
| 4,957,495 A | 9/1990 | Kluger et al. | |
| 4,987,892 A | 1/1991 | Krag et al. | |
| 5,005,562 A | 4/1991 | Cotrel et al. | |
| 5,042,982 A | 8/1991 | Harms et al. | |
| 5,067,955 A | 11/1991 | Cotrel | |
| 5,092,866 A | 3/1992 | Breard et al. | |
| 5,102,412 A | 4/1992 | Rogozinski | |
| 5,120,171 A | 6/1992 | Lasner | |
| 5,129,388 A | 7/1992 | Vignaud et al. | |
| 5,129,900 A | 7/1992 | Asher et al. | |
| 5,133,716 A | 7/1992 | Plaza | |
| 5,176,678 A | 1/1993 | Tsou | |
| 5,176,680 A | 1/1993 | Vignaud et al. | |
| 5,181,917 A | 1/1993 | Rogozinski | |
| 5,190,543 A | 3/1993 | Schlapfer | |
| 5,207,678 A | 5/1993 | Harms et al. | |
| 5,219,349 A | 6/1993 | Krag et al. | |
| 5,226,766 A | 7/1993 | Lasner | |
| 5,263,939 A | 11/1993 | Wortrich | |
| 5,282,801 A | 2/1994 | Sherman | |
| 5,282,863 A | 2/1994 | Burton | |
| 5,290,289 A | 3/1994 | Sanders et al. | |
| 5,312,404 A | 5/1994 | Asher et al. | |
| 5,330,473 A | 7/1994 | Howland | |
| 5,360,431 A | 11/1994 | Puno et al. | |
| 5,385,565 A | 1/1995 | Ray | |
| 5,387,212 A | 2/1995 | Yuan et al. | |
| 5,387,213 A | 2/1995 | Breard et al. | |
| 5,391,168 A | 2/1995 | Sanders et al. | |
| 5,413,576 A | 5/1995 | Rivard | |
| 5,415,661 A | 5/1995 | Holmes | |
| 5,437,669 A | 8/1995 | Yuan et al. | |
| 5,437,673 A | 8/1995 | Baust et al. | |
| 5,445,140 A | 8/1995 | Tovey | |
| 5,466,238 A | 11/1995 | Lin | |
| 5,468,241 A | 11/1995 | Metz-Stavenhagen et al. | |
| 5,487,742 A | 1/1996 | Cotrel | |
| 5,487,744 A | 1/1996 | Howland | |
| 5,499,983 A | 3/1996 | Hughes | |
| 5,501,684 A | 3/1996 | Schlapfer et al. | |
| 5,520,689 A | 5/1996 | Schlapfer et al. | |
| 5,536,127 A | 7/1996 | Pennig | |
| 5,536,268 A | 7/1996 | Griss | |
| 5,540,688 A | 7/1996 | Navas | |
| 5,540,689 A | 7/1996 | Sanders et al. | |
| 5,545,165 A | 8/1996 | Biedermann et al. | |
| 5,549,552 A | 8/1996 | Peters et al. | |
| 5,549,608 A | 8/1996 | Errico et al. | |
| 5,586,983 A | 12/1996 | Sanders et al. | |
| 5,591,166 A | 1/1997 | Bernhardt et al. | |
| 5,593,407 A | 1/1997 | Reis et al. | |
| 5,593,408 A | 1/1997 | Gayet et al. | |
| 5,597,378 A | 1/1997 | Jervis | |
| 5,601,552 A | 2/1997 | Cotrel | |
| 5,626,581 A | 5/1997 | Staehlin et al. | |
| 5,630,816 A | 5/1997 | Kambin | |
| 5,645,520 A | 7/1997 | Nakamura et al. | |
| 5,649,931 A | 7/1997 | Bryant et al. | |
| 5,651,789 A | 7/1997 | Cotrel | |
| 5,658,286 A | 8/1997 | Sava | |
| 5,667,513 A | 9/1997 | Torrie et al. | |
| 5,672,175 A | 9/1997 | Martin | |
| 5,672,176 A | 9/1997 | Biedermann et al. | |
| 5,702,452 A | 12/1997 | Argenson et al. | |
| 5,725,527 A | 3/1998 | Biedermann et al. | |
| 5,738,685 A | 4/1998 | Halm et al. | |
| 5,743,907 A | 4/1998 | Asher et al. | |
| 5,743,911 A | 4/1998 | Cotrel | |
| 5,766,004 A * | 6/1998 | Besselink et al. | 433/5 |
| 5,797,911 A | 8/1998 | Sherman et al. | |
| 5,830,179 A * | 11/1998 | Mikus et al. | 604/517 |
| 5,833,707 A * | 11/1998 | McIntyre et al. | 606/198 |
| 5,879,350 A | 3/1999 | Sherman et al. | |
| 5,882,350 A | 3/1999 | Ralph et al. | |
| 5,885,285 A | 3/1999 | Simonson | |
| 5,899,903 A | 5/1999 | Cotrel | |
| RE36,221 E | 6/1999 | Breard et al. | |
| 5,910,141 A | 6/1999 | Morrison et al. | |
| 5,910,142 A | 6/1999 | Tatar | |
| 5,919,158 A * | 7/1999 | Saperstein et al. | 600/500 |
| 5,947,965 A | 9/1999 | Bryan | |
| 5,947,966 A | 9/1999 | Drewry et al. | |
| 5,951,555 A | 9/1999 | Rehak et al. | |
| 5,961,515 A | 10/1999 | Taylor et al. | |
| 5,964,760 A | 10/1999 | Richelsoph | |
| 5,964,770 A | 10/1999 | Flomenblit et al. | |
| 5,977,580 A * | 11/1999 | Yoon | 257/306 |
| 5,989,250 A | 11/1999 | Wagner et al. | |
| 5,989,254 A | 11/1999 | Katz | |
| 5,997,580 A * | 12/1999 | Mastrorio et al. | 623/23.48 |
| 6,050,997 A | 4/2000 | Mullane | |
| 6,063,090 A | 5/2000 | Schlapfer | |
| 6,071,250 A | 6/2000 | Douglas et al. | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,113 A | 7/2000 | Le Couedic et al. | |
| 6,102,912 A | 8/2000 | Cazin et al. | |
| 6,106,527 A | 8/2000 | Wu et al. | |
| 6,110,172 A | 8/2000 | Jackson | |
| 6,127,597 A * | 10/2000 | Beyar et al. | 606/86 R |
| 6,139,548 A | 10/2000 | Errico | |
| 6,139,549 A | 10/2000 | Keller | |
| 6,146,383 A | 11/2000 | Studer et al. | |
| 6,183,472 B1 | 2/2001 | Lutz | |
| 6,200,317 B1 | 3/2001 | Aalsma et al. | |
| 6,204,060 B1 | 3/2001 | Mehtali et al. | |
| 6,214,006 B1 | 4/2001 | Metz-Stavenhagen | |
| 6,214,730 B1 | 4/2001 | Cooney, III et al. | |
| 6,235,028 B1 | 5/2001 | Brumfield et al. | |
| 6,238,491 B1 * | 5/2001 | Davidson et al. | 148/237 |
| 6,241,730 B1 | 6/2001 | Alby | |
| 6,254,602 B1 | 7/2001 | Justis | |
| 6,261,287 B1 | 7/2001 | Metz-Stavenhagen | |
| 6,261,288 B1 | 7/2001 | Jackson | |
| 6,267,764 B1 | 7/2001 | Elberg | |
| 6,273,914 B1 | 8/2001 | Papas | |
| 6,280,442 B1 | 8/2001 | Barker et al. | |
| 6,280,443 B1 | 8/2001 | Gu et al. | |
| 6,293,949 B1 | 9/2001 | Justis et al. | |
| 6,299,216 B1 | 10/2001 | Thompson | |
| 6,302,888 B1 | 10/2001 | Mellinger et al. | |
| 6,306,141 B1 * | 10/2001 | Jervis | 606/78 |
| 6,309,389 B1 | 10/2001 | Baccelli | |
| 6,309,391 B1 | 10/2001 | Crandall et al. | |
| 6,325,805 B1 | 12/2001 | Ogilvie et al. | |
| 6,328,741 B1 | 12/2001 | Richelsoph | |
| 6,361,637 B2 * | 3/2002 | Martin et al. | 156/187 |
| 6,368,321 B1 | 4/2002 | Jackson | |
| 6,379,357 B1 | 4/2002 | Bernstein et al. | |
| 6,389,710 B1 | 5/2002 | Chou | |
| 6,402,752 B2 | 6/2002 | Schaffler-Wachter et al. | |
| 6,423,065 B2 | 7/2002 | Ferree | |
| 6,440,133 B1 | 8/2002 | Beale et al. | |
| 6,440,137 B1 | 8/2002 | Horvath et al. | |
| 6,443,953 B1 | 9/2002 | Perra et al. | |
| 6,447,478 B1 * | 9/2002 | Maynard | 604/95.05 |
| 6,471,716 B1 | 10/2002 | Pecukonis | |
| 6,478,798 B1 | 11/2002 | Howland | |
| 6,485,491 B1 | 11/2002 | Farris et al. | |
| 6,485,492 B1 | 11/2002 | Halm et al. | |
| 6,517,533 B1 * | 2/2003 | Swaminathan | 606/20 |
| 6,520,962 B1 | 2/2003 | Taylor et al. | |
| 6,537,276 B2 | 3/2003 | Metz-Stavenhagen | |
| 6,540,748 B2 | 4/2003 | Lombardo | |
| 6,540,749 B2 | 4/2003 | Schafer et al. | |
| 6,551,320 B2 | 4/2003 | Lieberman | |
| 6,554,834 B1 | 4/2003 | Crozet et al. | |
| 6,565,567 B1 | 5/2003 | Haider | |
| 6,597,279 B1 | 7/2003 | Haraguchi | |
| 6,616,669 B2 | 9/2003 | Ogilvie et al. | |
| 6,623,485 B2 | 9/2003 | Doubler et al. | |
| 6,648,888 B1 | 11/2003 | Shluzas | |
| 6,652,526 B1 | 11/2003 | Arafiles | |
| 6,660,006 B2 | 12/2003 | Markworth et al. | |
| 6,689,137 B2 | 2/2004 | Reed | |

| | | | | | | |
|---|---|---|---|---|---|---|
| 6,692,500 B2 | 2/2004 | Reed | | 8,075,591 B2 | 12/2011 | Ludwig et al. |
| 6,695,843 B2 | 2/2004 | Biedermann et al. | | 2001/0020169 A1 | 9/2001 | Metz-Stavenhagen |
| 6,706,044 B2 | 3/2004 | Kuslich et al. | | 2002/0032442 A1 | 3/2002 | Altarac et al. |
| 6,716,214 B1 | 4/2004 | Jackson | | 2002/0035366 A1 | 3/2002 | Walder et al. |
| 6,730,087 B1 | 5/2004 | Butsch | | 2002/0082599 A1 | 6/2002 | Crandall et al. |
| 6,733,502 B2 | 5/2004 | Altarac et al. | | 2002/0133155 A1 | 9/2002 | Ferree |
| 6,733,531 B1 * | 5/2004 | Trieu .................. 623/17.11 | | 2002/0138077 A1 | 9/2002 | Ferree |
| 6,743,231 B1 | 6/2004 | Gray et al. | | 2002/0143327 A1 | 10/2002 | Shluzas |
| 6,749,613 B1 | 6/2004 | Conchy et al. | | 2002/0143341 A1 | 10/2002 | Biedermann et al. |
| 6,755,829 B1 | 6/2004 | Bono et al. | | 2002/0169449 A1 | 11/2002 | Kuslich et al. |
| 6,761,719 B2 | 7/2004 | Justis et al. | | 2002/0173789 A1 | 11/2002 | Howland |
| 6,783,527 B2 | 8/2004 | Drewry et al. | | 2003/0004512 A1 | 1/2003 | Farris et al. |
| 6,786,984 B1 * | 9/2004 | Hanada et al. ............. 148/421 | | 2003/0023240 A1 | 1/2003 | Amrein et al. |
| 6,800,078 B2 | 10/2004 | Reed | | 2003/0073995 A1 | 4/2003 | Reed |
| 6,800,079 B2 | 10/2004 | Reed | | 2003/0083657 A1 | 5/2003 | Drewry et al. |
| 6,800,778 B1 | 10/2004 | Aoki et al. | | 2003/0088248 A1 | 5/2003 | Reed |
| 6,802,844 B2 | 10/2004 | Ferree | | 2003/0100896 A1 | 5/2003 | Biedermann et al. |
| 6,837,889 B2 | 1/2005 | Shluzas | | 2003/0105460 A1 | 6/2003 | Crandall et al. |
| 6,872,208 B1 | 3/2005 | McBride et al. | | 2003/0109880 A1 | 6/2003 | Shirado et al. |
| 6,881,220 B2 * | 4/2005 | Edwin et al. ............... 623/1.11 | | 2003/0114853 A1 | 6/2003 | Burgess et al. |
| 6,887,241 B1 | 5/2005 | McBride et al. | | 2003/0171749 A1 | 9/2003 | Le Couedic et al. |
| 6,964,666 B2 | 11/2005 | Jackson | | 2003/0176861 A1 | 9/2003 | Reed |
| 6,984,242 B2 * | 1/2006 | Campbell et al. ............ 623/1.12 | | 2003/0191470 A1 | 10/2003 | Ritland |
| 6,986,771 B2 | 1/2006 | Paul et al. | | 2003/0203488 A1 | 10/2003 | Mehtali et al. |
| 6,989,011 B2 | 1/2006 | Paul et al. | | 2003/0220642 A1 | 11/2003 | Freudiger |
| 7,010,866 B1 | 3/2006 | Lin | | 2003/0220643 A1 | 11/2003 | Ferree |
| 7,044,966 B2 * | 5/2006 | Svanidze et al. .............. 623/2.1 | | 2004/0002708 A1 | 1/2004 | Ritland |
| 7,044,982 B2 * | 5/2006 | Milbocker ................. 623/23.72 | | 2004/0049189 A1 | 3/2004 | Le Couedic et al. |
| 7,063,706 B2 | 6/2006 | Wittenstein | | 2004/0049190 A1 | 3/2004 | Biedermann et al. |
| 7,066,938 B2 | 6/2006 | Slivka et al. | | 2004/0073215 A1 | 4/2004 | Carli |
| 7,094,237 B2 | 8/2006 | Gradel et al. | | 2004/0106921 A1 | 6/2004 | Cheung et al. |
| 7,104,993 B2 | 9/2006 | Baynham et al. | | 2004/0158258 A1 | 8/2004 | Bonati et al. |
| 7,125,410 B2 | 10/2006 | Freudiger | | 2004/0162558 A1 | 8/2004 | Hegde et al. |
| 7,128,743 B2 | 10/2006 | Metz-Stavenhagen | | 2004/0172020 A1 | 9/2004 | Beaurain et al. |
| 7,128,758 B2 * | 10/2006 | Cox ......................... 623/1.19 | | 2004/0172025 A1 | 9/2004 | Drewry et al. |
| 7,179,261 B2 | 2/2007 | Sicvol et al. | | 2004/0181224 A1 | 9/2004 | Biedermann et al. |
| 7,207,986 B2 * | 4/2007 | Abboud et al. ................. 606/20 | | 2004/0186472 A1 | 9/2004 | Lewis et al. |
| 7,267,687 B2 * | 9/2007 | McGuckin, Jr. ........... 623/17.11 | | 2004/0186473 A1 | 9/2004 | Cournoyer et al. |
| 7,322,979 B2 | 1/2008 | Crandall et al. | | 2004/0204711 A1 | 10/2004 | Jackson |
| 7,335,200 B2 | 2/2008 | Carli | | 2004/0215191 A1 | 10/2004 | Kitchen |
| 7,377,923 B2 | 5/2008 | Purcell et al. | | 2004/0225289 A1 | 11/2004 | Biedermann et al. |
| 7,381,625 B2 * | 6/2008 | Xi et al. ...................... 438/432 | | 2004/0236330 A1 | 11/2004 | Purcell et al. |
| 7,429,042 B2 * | 9/2008 | Ban et al. .................... 271/274 | | 2004/0254577 A1 | 12/2004 | Delecrin et al. |
| 7,442,192 B2 * | 10/2008 | Knowlton .................... 606/45 | | 2004/0260285 A1 | 12/2004 | Steib et al. |
| 7,455,685 B2 | 11/2008 | Justis | | 2004/0267260 A1 | 12/2004 | Mack et al. |
| 7,459,042 B2 * | 12/2008 | Parker ........................ 148/676 | | 2004/0267275 A1 | 12/2004 | Cournoyer et al. |
| 7,465,306 B2 | 12/2008 | Pond, Jr. et al. | | 2005/0010216 A1 | 1/2005 | Gradel et al. |
| 7,473,267 B2 | 1/2009 | Nguyen et al. | | 2005/0010233 A1 | 1/2005 | Wittenstein |
| 7,481,827 B2 | 1/2009 | Ryan et al. | | 2005/0010778 A1 | 1/2005 | Walmsley |
| 7,491,218 B2 | 2/2009 | Landry et al. | | 2005/0033291 A1 | 2/2005 | Ebara |
| 7,494,488 B2 * | 2/2009 | Weber ............................ 606/2 | | 2005/0033295 A1 | 2/2005 | Wisnewski |
| 7,507,248 B2 | 3/2009 | Beaurain et al. | | 2005/0038430 A1 | 2/2005 | McKinley |
| 7,559,942 B2 | 7/2009 | Paul et al. | | 2005/0065514 A1 | 3/2005 | Studer |
| 7,588,575 B2 | 9/2009 | Colleran et al. | | 2005/0065515 A1 | 3/2005 | Jahng |
| 7,604,653 B2 | 10/2009 | Kitchen | | 2005/0065516 A1 | 3/2005 | Jahng |
| 7,621,912 B2 | 11/2009 | Harms et al. | | 2005/0070899 A1 | 3/2005 | Doubler et al. |
| 7,632,292 B2 | 12/2009 | Sengupta et al. | | 2005/0070917 A1 | 3/2005 | Justis |
| 7,635,380 B2 | 12/2009 | Zucherman et al. | | 2005/0085815 A1 | 4/2005 | Harms et al. |
| 7,641,673 B2 | 1/2010 | Le Couedic et al. | | 2005/0107788 A1 | 5/2005 | Beaurain et al. |
| 7,658,739 B2 | 2/2010 | Shluzas | | 2005/0124991 A1 | 6/2005 | Jahng |
| 7,666,189 B2 | 2/2010 | Gerber et al. | | 2005/0131408 A1 | 6/2005 | Sicvol et al. |
| 7,691,145 B2 | 4/2010 | Reiley et al. | | 2005/0131422 A1 | 6/2005 | Anderson et al. |
| 7,699,872 B2 | 4/2010 | Farris et al. | | 2005/0149020 A1 | 7/2005 | Jahng |
| 7,749,258 B2 | 7/2010 | Biedermann et al. | | 2005/0154390 A1 | 7/2005 | Biedermann et al. |
| 7,763,048 B2 | 7/2010 | Fortin et al. | | 2005/0159650 A1 | 7/2005 | Raymond et al. |
| 7,763,049 B2 | 7/2010 | Roychowdhury | | 2005/0171538 A1 | 8/2005 | Sgier et al. |
| 7,766,944 B2 | 8/2010 | Metz-Stavenhagen | | 2005/0177157 A1 | 8/2005 | Jahng |
| 7,776,071 B2 | 8/2010 | Fortin et al. | | 2005/0192573 A1 | 9/2005 | Abdelgany et al. |
| 7,780,706 B2 | 8/2010 | Marino et al. | | 2005/0192589 A1 | 9/2005 | Raymond et al. |
| 7,789,897 B2 | 9/2010 | Sanders | | 2005/0203511 A1 | 9/2005 | Wilson-MacDonald et al. |
| 7,794,476 B2 | 9/2010 | Wisnewski | | 2005/0203518 A1 | 9/2005 | Biedermann et al. |
| 7,927,353 B2 | 4/2011 | Taylor et al. | | 2005/0222570 A1 | 10/2005 | Jackson |
| 7,976,568 B2 | 7/2011 | Cheung et al. | | 2005/0222683 A1 | 10/2005 | Berry |
| 7,988,713 B2 | 8/2011 | Metz-Stavenhagen | | 2005/0228376 A1 | 10/2005 | Boomer et al. |
| 8,002,806 B2 | 8/2011 | Justis | | 2005/0228378 A1 | 10/2005 | Kalfas et al. |
| 8,007,520 B2 | 8/2011 | Metz-Stavenhagen | | 2005/0228379 A1 | 10/2005 | Jackson |
| 8,021,389 B2 | 9/2011 | Molz, IV | | 2005/0240265 A1 * | 10/2005 | Kuiper et al. .............. 623/17.11 |
| 8,048,127 B2 | 11/2011 | Moulin et al. | | 2005/0245928 A1 | 11/2005 | Colleran et al. |
| 8,048,133 B2 | 11/2011 | Biedermann et al. | | 2005/0261687 A1 | 11/2005 | Garamszegi et al. |

| US Patent Application Publications | | | | Foreign Patent Documents | | |
|---|---|---|---|---|---|---|
| 2005/0261770 A1* | 11/2005 | Kuiper et al. ............... 623/17.11 | DE | 4330837 A1 | 3/1995 |
| 2005/0277932 A1 | 12/2005 | Farris | DE | 10005385 | 8/2001 |
| 2005/0283244 A1 | 12/2005 | Gordon | DE | 10005386 A1 | 8/2001 |
| 2005/0288668 A1 | 12/2005 | Brinkhaus | DE | 20207851 U1 | 11/2002 |
| 2006/0009767 A1 | 1/2006 | Kiester | DE | 102004010844 A1 | 10/2005 |
| 2006/0015527 A1 | 1/2006 | Dingle | EP | 0134622 A2 | 3/1985 |
| 2006/0025769 A1 | 2/2006 | Dick et al. | EP | 0140790 B1 | 5/1985 |
| 2006/0036255 A1 | 2/2006 | Pond et al. | EP | 0167703 B1 | 1/1986 |
| 2006/0064090 A1 | 3/2006 | Park | EP | 328883 B1 | 8/1989 |
| 2006/0111715 A1 | 5/2006 | Jackson | EP | 0330881 B1 | 9/1989 |
| 2006/0149228 A1 | 7/2006 | Schlapfer et al. | EP | 0381588 B1 | 8/1990 |
| 2006/0149236 A1 | 7/2006 | Barry | EP | 0446092 B1 | 9/1991 |
| 2006/0149237 A1 | 7/2006 | Markworth et al. | EP | 0470660 B1 | 2/1992 |
| 2006/0149240 A1 | 7/2006 | Jackson | EP | 0558883 A1 | 9/1993 |
| 2006/0155277 A1 | 7/2006 | Metz-Stavenhagen | EP | 0564046 B1 | 10/1993 |
| 2006/0161152 A1 | 7/2006 | Ensign et al. | EP | 0592266 A1 | 4/1994 |
| 2006/0173454 A1 | 8/2006 | Spitler et al. | EP | 0669109 A1 | 8/1995 |
| 2006/0184171 A1 | 8/2006 | Biedermann et al. | EP | 784693 B1 | 7/1997 |
| 2006/0195092 A1 | 8/2006 | Barry | EP | 0811357 A1 | 12/1997 |
| 2006/0200129 A1 | 9/2006 | Denti | EP | 0846444 A1 | 6/1998 |
| 2006/0200131 A1 | 9/2006 | Chao et al. | EP | 0879579 B1 | 11/1998 |
| 2006/0200132 A1 | 9/2006 | Chao et al. | EP | 0880344 B1 | 12/1998 |
| 2006/0206114 A1 | 9/2006 | Ensign et al. | EP | 0885598 B1 | 12/1998 |
| 2006/0217735 A1 | 9/2006 | MacDonald et al. | EP | 0951246 B1 | 10/1999 |
| 2006/0229607 A1 | 10/2006 | Brumfield | EP | 1023873 B1 | 8/2000 |
| 2006/0229614 A1 | 10/2006 | Foley et al. | EP | 1295566 A1 | 3/2003 |
| 2006/0229615 A1* | 10/2006 | Abdou ............... 606/61 | EP | 1302169 B1 | 4/2003 |
| 2006/0235389 A1 | 10/2006 | Albert et al. | EP | 1774919 B1 | 4/2007 |
| 2006/0240533 A1 | 10/2006 | Sengupta et al. | EP | 1937168 B1 | 7/2008 |
| 2006/0264935 A1 | 11/2006 | White | FR | 2624720 A1 | 6/1989 |
| 2006/0264937 A1 | 11/2006 | White | FR | 2759894 A1 | 8/1998 |
| 2006/0271193 A1 | 11/2006 | Hartmann et al. | FR | 2763831 A1 | 12/1998 |
| 2006/0282073 A1 | 12/2006 | Simanovsky | FR | 2786088 A1 | 5/2000 |
| 2007/0016201 A1 | 1/2007 | Freudiger | FR | 2806615 A1 | 9/2001 |
| 2007/0049937 A1 | 3/2007 | Matthis et al. | FR | 2813782 A1 | 3/2002 |
| 2007/0055240 A1 | 3/2007 | Matthis et al. | FR | 2835735 A1 | 8/2003 |
| 2007/0090238 A1 | 4/2007 | Justis | FR | 2839880 A1 | 11/2003 |
| 2007/0161990 A1 | 7/2007 | Hillyard et al. | GB | 2412320 | 9/2005 |
| 2007/0161994 A1 | 7/2007 | Lowery et al. | NL | 7205928 | 11/1973 |
| 2007/0162007 A1 | 7/2007 | Shoham | WO | 90/02527 A1 | 3/1990 |
| 2007/0162009 A1 | 7/2007 | Chao et al. | WO | 91/19469 A1 | 12/1991 |
| 2007/0162010 A1 | 7/2007 | Chao et al. | WO | 95/09578 A1 | 4/1995 |
| 2007/0173800 A1 | 7/2007 | Sanders et al. | WO | 97/31580 A1 | 9/1997 |
| 2007/0173828 A1* | 7/2007 | Firkins et al. ............... 606/61 | WO | 98/22033 A1 | 5/1998 |
| 2007/0179501 A1* | 8/2007 | Firkins ............... 606/61 | WO | 99/00065 A1 | 1/1999 |
| 2007/0191831 A1 | 8/2007 | Sanders et al. | WO | 99/44527 A1 | 9/1999 |
| 2007/0191841 A1 | 8/2007 | Justis et al. | WO | 01/45576 A1 | 6/2001 |
| 2007/0191842 A1 | 8/2007 | Molz et al. | WO | 01/57801 A2 | 8/2001 |
| 2007/0198088 A1 | 8/2007 | Biedermann et al. | WO | 01/91656 A2 | 12/2001 |
| 2007/0213721 A1 | 9/2007 | Markworth et al. | WO | 02/07622 A1 | 1/2002 |
| 2007/0213723 A1 | 9/2007 | Markworth et al. | WO | 02/22030 A2 | 3/2002 |
| 2007/0239154 A1 | 10/2007 | Shaolian et al. | WO | 02/34149 A2 | 5/2002 |
| 2007/0270843 A1 | 11/2007 | Matthis et al. | WO | 02/34310 A2 | 5/2002 |
| 2007/0288013 A1 | 12/2007 | Sanders | WO | 02/080788 A1 | 10/2002 |
| 2008/0021456 A1 | 1/2008 | Gupta et al. | WO | 02/102259 A2 | 12/2002 |
| 2008/0027436 A1 | 1/2008 | Cournoyer et al. | WO | 03/007828 A1 | 1/2003 |
| 2008/0058805 A1 | 3/2008 | Stuart | WO | 03/037198 A1 | 5/2003 |
| 2008/0071373 A1* | 3/2008 | Molz et al. ............... 623/17.11 | WO | 03/049629 A1 | 6/2003 |
| 2008/0114404 A1 | 5/2008 | Matthis et al. | WO | 2004/017705 A2 | 3/2004 |
| 2008/0195159 A1 | 8/2008 | Kloss et al. | WO | 2004/019755 A2 | 3/2004 |
| 2008/0234756 A1 | 9/2008 | Sutcliffe et al. | WO | 2004/034916 A1 | 4/2004 |
| 2008/0243189 A1 | 10/2008 | Purcell et al. | WO | 2004/041100 A1 | 5/2004 |
| 2008/0269805 A1 | 10/2008 | Dekutoski et al. | WO | 2004/073534 A1 | 9/2004 |
| 2009/0048632 A1 | 2/2009 | Firkins et al. | WO | 2004/096066 A2 | 11/2004 |
| 2009/0182381 A1 | 7/2009 | Beaurain et al. | WO | 2004/103194 A1 | 12/2004 |
| 2009/0198280 A1 | 8/2009 | Spratt et al. | WO | 2004/105577 A2 | 12/2004 |
| 2009/0222042 A1 | 9/2009 | Firkins et al. | WO | 2005/013839 A2 | 2/2005 |
| 2010/0010547 A1 | 1/2010 | Beaurain et al. | WO | 2005/030065 A1 | 4/2005 |
| 2010/0042156 A1 | 2/2010 | Harms et al. | WO | 2005/044117 A2 | 5/2005 |
| 2010/0063548 A1 | 3/2010 | Wang | WO | 2005/044123 A1 | 5/2005 |
| 2010/0114169 A1 | 5/2010 | Le Couedic et al. | WO | 2005/097006 A2 | 10/2005 |
| 2010/0114173 A1 | 5/2010 | Le Couedic et al. | WO | 2005/122927 A1 | 12/2005 |
| 2010/0249848 A1 | 9/2010 | Wisnewski | WO | 2006/084443 A1 | 8/2006 |
| | | | WO | 2006/101898 A1 | 9/2006 |
| FOREIGN PATENT DOCUMENTS | | | WO | 2006/130179 A2 | 12/2006 |
| DE | 4107480 A1 | 9/1992 | WO | 2007/019204 A2 | 2/2007 |
| DE | 9218381.6 U1 | 4/1994 | WO | 2007/041265 A1 | 4/2007 |
| DE | 9314297.8 U1 | 5/1994 | WO | 2007/045892 A1 | 4/2007 |
| DE | 9402695.5 U1 | 5/1994 | WO | 2007/045899 A1 | 4/2007 |

| | | | |
|---|---|---|---|
| WO | 2007/047711 A2 | 4/2007 |
| WO | 2007/089984 A2 | 8/2007 |
| WO | 2007/121030 A1 | 10/2007 |
| WO | 2007/138190 A2 | 12/2007 |
| WO | 2008/000944 A2 | 1/2008 |

OTHER PUBLICATIONS

Brymill Cryogenic Systems, "CRY-AC & CRY-AC-3," retrieved online at: http://www.brymill.com/catalog_1_cyrac.htm (2010).
Chemtronics, Technical Data Sheet, "Freez-It Freeze Spray," TDS#1550E, Aug. 4, 2005.
GHS Medical, "Our Light Coagulator Product Family," retrieved online at: http://www/ghs-medical.com/geraeteha02.htm (2005).
NDC, Nitinol Devices & Components, "Nitinol Technology," retrieved online at: http://www.nitinol.com/3tech.htm (2001).
Niti Smart Sheet, retrieved online at: http://www.sma.inc.com (2001).
Veldhuizen, A.G. et al., "A scoliosis correction device based on memory metal," Med. Eng. Phys., vol. 19 (2):171-179 (1997).
Wever, D.J. et al., "Scoliosis correction with shape-memory metal: results of an experimental study," Eur. Spine J., vol. 11:100-106 (2002).
Denkhaus, E. et al., "Nickel essentiality, toxicity, and carcinogenicity," Critical Reviews in Oncology/Hematology, vol. 42:35-56 (2002).
Lu, "Treatment of scoliosis with a shape-memory alloy rod," Zhonghua Wai Ke Za Zhi, vol. 24(3):129-132 (1986).
Andreasen, G., "A clinical trial of alignment of teeth using a 0.019 inch thermal nitinol wire with a transition temperature range between 31 degree C. and 45 degrees C.," Am. J. Orthod., vol. 78(5):528-537 (1980) Abstract Only.
Asher, Marc A. et al., "Adolescent idiopathic scoliosis: natural history and long term treatment effects," Scoliosis, vol. 1(2):1-10 doi:10.1186/1748-7161-1-2 (2006).
Betz, Randal R. et al., "An Innovative Technique of Vertebral Body Stapling for the Treatment of Patients With Adolescent Idiopathic Scoliosis: A Feasibility, Safety, and Utility Study," Spine, vol. 28(20S):S255-S265 (2003).
Bischoff, Robert et al., "The Use of Texas Scottish-Rite Instrumentation in Idiopathic Scoliosis," Spine, vol. 18(16):2452-2456 (1993).
Boos, N. et al., "Pedicle screw fixation in spinal disorders: a European view," Eur. Spine J. vol. 6:2-18 (1997).
Braun, John T. et al., "Fusionless Scoliosis Correction Using a Shape Memory Alloy Staple in the Anterior Thoracic Spine of the Immature Goat," Spine, vol. 29(18):1980-1989 (2004).
Braun, John T. et al., "Mechanical Modulation of Vertebral Growth in the Fusionless Treatment of Progressive Scoliosis in an Experimental Model," Spine, vol. 31(12):1314-1320 (2006).
Braun, John T. et al., "Relative Versus Absolute Modulation of Growth in the Fusionless Treatment of Experimental Scoliosis," Spine, vol. 31(16):1776-1782 (2006).
Bridwell, Keith H., "Surgical Treatment of Idiopathic Adolescent Scoliosis," Spine, vol. 24(24):2607-2616 (1999).
Cotrel, Y. et al., "New Universal Instrumentation in Spinal Surgery," Clin. Orthop. Relat. Res., vol. 227:10-23 (1988).
Goshi, Kohei et al., "Thoracic scoliosis fusion in adolescent and adult idiopathic scoliosis using posterior translational corrective techniques (Isola): is maximum correction of the thoracic curve detrimental to the unfused lumbar curve?" The Spine Journal, vol. 4:192-201 (2004).
Halm, H. et al., "Segmental pedicle screw instrumentation in idiopathic thoracolumbar and lumbar scoliosis," Eur. Spine J., vol. 9:191-197 (2000).
Hamill, Christopher L. et al., "The Use of Pedicle Screw Fixation to Improve Correction in teh Lumbar Spine in Patients Witih Idiopathic Scoliosis: Is It Warranted?" Spine, vol. 21(10):1241-1249 (1996).
Harrington, Paul R. et al., "Treatment of Scoliosis," The Journal of Bone and Joint Surgery, American Volume, vol. 44-A(4):591-634 (1962).
Kim, Yongjung J. et al., "Comparative Analysis of Pedicle Screw Versus Hybrid Instrumentation in Posterior Spinal Fusion of Adolescent Idiopathic Scoliosis," Spine, vol. 31(3):291-298 (2006).
Lehman, Ronald A. et al., "Straight-Forward Versus Anatomic Trajectory Technique of Thoracic Pedicle Screw Fixation: a Biomechanical Analysis," Spine, vol. 28(18):2058-2065 (2003).
Liljenqvist, Ulf R. et al., "Pedicle Screw Instrumentation of the Thoracic Spine in Idiopathic Scoliosis," Spine, vol. 22(19):2239-2245 (1997).
Liu, X. M. et al."Surface characteristics, biocompatibility, and mechanical properties of nickel-titanium plasma-implanted with nitrogen at different implantation voltages," J. Biomed. Mater Res. A., vol. 82(2):469-478 (2007).
Matsumoto, K. et al., "Correction of scoliosis with shape-memory alloy," Nippon Seikeigeka Gakkai Zasshi, vol. 67 (4):267-274 (1993) Abstract Only.
Misenhimer, G.R. et al., "Anatomic Analysis of Pedicle Cortical and Cancellous Diameter as Related to Screw Size," Spine, vol. 14(4):367-372 (1989).
Puttlitz, Christian M. et al., "A Biomechanical Assessment of Thoracic Spine Stapling," Spine, vol. 32(7):766-771 (2007).
Sanders, James O. et al., "A Preliminary Investigation of Shape Memory Alloys in the Surgical Correction of Scoliosis," Spine, vol. 18(12):1640-1646 (1993).
Shabalovskaya, Svetlana, "Surface, corrosion and biocompatibility aspects of Nitinol as an implant material," Bio-Medical Materials and Engineering, vol. 12:69-109 (2002).
Steinmann, John C. et al., "Spinal Pedicle Fixation, Confirmation of an Image-Based Technique for Screw Placement," Spine, vol. 18(13)1856-1861 (1993).
Suk, Se-Il et al., "Segmental Pedicle Screw Fixation in the Treatment of Thoracic Idiopathic Scoliosis," Spine, vol. 20 (12):1399-1405 (1995).
Suk, Se-Il et al., "Thoracic Pedicle Screw Fixation in Spinal Deformities, Are They Really Safe?" Spine, vol. 26 (18):2049-2057 (2001).
Szold, A., "Nitinol: shape-memory and super-elastic materials in surgery," Surg. Endosc., vol. 20:1493-1496 (2006).
Takeshita, K. et al., "Correction of scoliosis using segmental pedicle scres instrumentation versus hybrid constructs with hooks and screws," Stud. Health Technol. Inform., vol. 123:571-576 (2006) Abstract Only.
Wang, A. et al., "Experimental study of recovery force of surface-modified TiNi memory alloy rod," Sheng Wu Yi Xue Gong Cheng Xue Za Zhi, vol. 23(4):774-777 (2006) Abstract Only.
Wiltse, Leon L, "History of Pedicle Screw Fixation of the Spine," Spine: State of the Art Reviews, vol. 6(1):1-10 (1992).
Wu, Shuilin et al., "Nickel release behavior, cytocompatibility, and superelasticity of oxidized porous single-phase NiTi," J. Biomed. Mater. Res. A., vol. 81(4):948-955 (2007).
Yeung, K.W.K. et al., "Surface mechanical properties, corrosion resistance, and cytocompatibility of nitrogen plasma-implanted nickel-titanium alloys: a comparative study with commonly used medical grade materials," J. Biomed. Mater. Res. A., vol. 82(2):403-414 (2007).
Zdeblick, Thomas A. et al., "Anterior Spinal Fixation After Lumbar Corpectomy," The Journal of Bone and Joint Surgery, vol. 73-A(4):527-534 (1991).
Zindrick, Michael R. et al., "Pedicle Morphology of the Immature Thoracolumbar Spine," Spine, vol. 25 (21):2726-2735 (2000).
European Office Action for Application No. 06736870.4, 10 pages, dated Dec. 18, 2009.
International Search Report for Application No. PCT/US06/05811, 3 pages, dated Sep. 13, 2007.
International Search Report for Application No. PCT/US06/40621, 1 page, dated May 18, 2007.

* cited by examiner

SYSTEM AND METHOD FOR COOLING A SPINAL CORRECTION DEVICE COMPRISING A SHAPE MEMORY MATERIAL FOR CORRECTIVE SPINAL SURGERY

FIELD OF THE INVENTION

The present invention relates to spinal correction devices used in corrective spinal surgery. More particularly, the present invention relates to devices and methods for cooling a spinal correction device that is used in a corrective spinal surgery to transition a shape memory material in a spinal correction element from an austenitic state to a flexible martensitic state to allow shaping of the spinal correction element.

BACKGROUND OF THE INVENTION

Spinal corrective systems may be used in orthopedic surgery to correct a deformity or misalignment in the spinal column, as well as stabilize and/or fix a desired relationship between adjacent vertebral bodies. Spinal corrective surgery may be used to correct a variety of defects in the spine, such as scoliosis, spondylosis, spondylolisthesis, vertebral instability, spinal stenosis, degenerated, herniated, or degenerated and herniated intervertebral discs, as well as injuries, including fractures and torn ligaments and surgical manipulations, including laminectomies.

In spinal corrective surgery, a spinal corrective device, such as a spinal rod, and bone anchors, such as screws, bolts, wires and/or hooks, may be used to stabilize the spine, repair a defect and/or bring misaligned vertebrae back into alignment and secure the aligned vertebrae in the aligned position. A standard surgical procedure for correcting spinal defects in the current state of the art involves first distracting the vertebrae, pulling the vertebra back into alignment with the spinal column, and then stabilizing the spine using posterior spinal implants consisting of anchoring devices and spinal corrective elements. An interbody fusion device may also be used to give further stability and correction of the disc height. Compression across the vertebrae may be applied across the construct to set the correct balance of forces in the region.

A spinal corrective device used in such systems is generally a relatively rigid fixation rod or plate that is coupled to a bone by attaching the element to various anchoring devices. The corrective device can extend between two bone regions to effect stabilization, positioning, reduction and/or fixation of the bones. The spinal corrective device can have a predetermined contour that has been designed according to the properties of the target implantation site and, once installed, the spinal corrective element holds the bones in a desired spatial relationship, either until desired healing or spinal fusion has occurred, or for some longer period of time.

Shape memory materials have been used in spinal corrective systems to apply corrective forces to the spine by transitioning a shape memory material in a spinal corrective device between a flexible martensitic state and a rigid austenitic state to generate corrective forces that are transferred to the spine. Shape memory materials are characterized by an ability to restore the material to a pre-selected shape of the austenitic state after plastic deformation. For example, in an austenitic state, the shape memory material is stiff, rigid and has a set, pre-selected shape. In a martensitic state, the shape memory material becomes flexible and deformable and may have any of a variety of shapes. The microstructure of the material in the martensitic state is characterized by "self-accommodating twins", having a zigzag arrangement, which allow for deformation of the material shape by de-twinning.

Generally, shape memory materials are induced to transition between the rigid austenitic state and the flexible martensitic state by changing the temperature, pressure, stress, chemistry and/or another parameter of the shape memory material. For example, a shape memory material may be cooled to make the material flexible in a martensite state, and subsequently heated to return the material to the original shape with the austenitic structure. The temperature at which a shape memory material starts transforming to austenite is known as the "austenite start temperature." Further heating increases the temperature of the shape memory material to induce a complete transformation to the austenitic state, setting the shape of the material in the pre-selected shape of the austenitic structure. The temperature at which a shape memory material finishes transforming to austenite is known as the "austenite finish temperature." A shape memory material can transition to the martensitic state to allow deformation and shaping of the spinal corrective device by changing the temperature of the material below a selected temperature (i.e., cooling the material). The temperature at which a shape memory material begins transformation to the martensite state is known as the "martensite start temperature". Further cooling decreases the temperature of the shape memory material to induce a complete transformation to the martensite state. The temperature at which a shape memory material finishes transformation to the martensite state is known as the "martensite finish temperature."

Performing cooling of shape memory material in spinal corrective devices, such as spinal rods, from an ambient or heated state prior to implantation or following implantation can be problematic. For example, the process of handling, manipulating and implanting the spinal corrective device may create a heating effect, causing the device to transition from the martensitic state to the austenitic state before it is desirable. Shape memory corrective devices should therefore be cooled thoroughly to give maximum useful operating time.

SUMMARY OF THE INVENTION

The present invention provides system and method for cooling a spinal correction device, such as a spinal rod, to a martensitic state to allow shaping and manipulation of the spinal correction device during a spinal corrective surgery. The system and method may comprise applying a coolant, such as cold gas, directly or indirectly to the material to transfer heat away from the material to induce the transition to a martensitic state. The system and method may allow for in-vivo shaping of the spinal correction device while inserted in the body and attached to bone anchors by cooling the spinal correction device after insertion.

According to one aspect of the invention, a method of cooling a spinal correction device comprising a shape memory material comprises the steps of providing a spinal correction device comprised at least partially of a shape memory material and using a cold gas to the spinal correction device to transition at least a portion of the shape memory material from an austenitic state to a martensitic state.

According to another aspect of the invention, a method of correcting a spinal deformity comprises the steps of placing a cooled spinal correction device in the body, wherein the cooled spinal correction device includes a shape memory material, and cooling the spinal correction device while in the body to transition the shape memory material to a martensitic state.

According to still another aspect of the invention, a cooling system for a spinal correction device comprises a housing defining an insulated chamber for receiving a spinal correction device comprising a shape memory material, a source of cooling gas for cooling the insulated chamber to cool the shape memory material and a valve for selectively coupling the source of gas to the insulated chamber to controllably inject cooling gas into the insulated chamber.

In still another aspect of the invention, a method of cooling a spinal correction device comprising a shape memory alloy comprises providing a spinal correction device comprising a shape memory material and cooling a first segment of the spinal correction device without affecting the temperature of other segments of the spinal correction device.

BRIEF DESCRIPTION OF THE FIGURES

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions

DETAILED DESCRIPTION OF THE INVENTION

The present invention provides an improved surgical device and method for correcting a spinal defect in a patient. The present invention will be described below relative to certain exemplary embodiments to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein.

Figure 1:
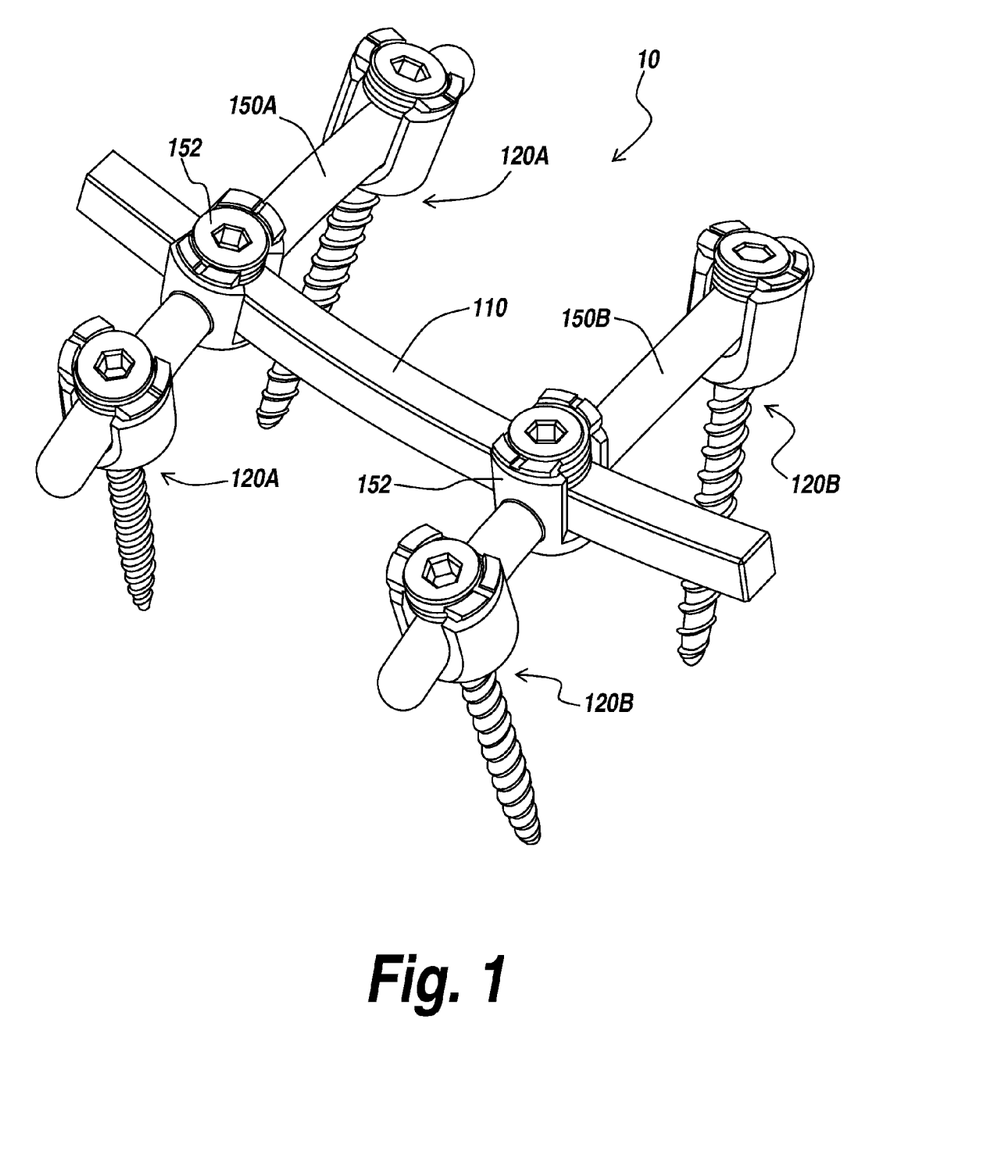
FIG. 1 illustrates a spinal correction system according to one embodiment of the invention.

FIG. 1 illustrates a spinal correction system 10 suitable for performing a spinal corrective surgery according to an illustrative embodiment of the invention. The spinal correction system preferably includes a plurality of bone anchors, illustrated as bone screws 120, and one or more spinal corrective devices, illustrated as a spinal rod 110, for attaching to the bone anchors 120 and applying a corrective force to move the spine to a corrected shape. A first set of bone screws 120A is attached to and straddles a first vertebra, and a second set of bone screws 120B is attached to and straddles a second vertebra. Bridges 150A and 150B extend between each pair of bone screws 120A, 120B, respectively, each including a rod-receiving portion 152 for receiving the spinal rod 110 to connect the spinal rod 110 to the bone anchors and vertebrae. Locking mechanism may be provided to secure the bridges 150A, 150B to the bone anchors and the spinal corrective device to the bridges 150. Such components are known in the art and may have any suitable size, shape and configuration. Several pairs of bone anchors and bridges may be used to connect the spinal corrective device across a number of vertebrae.

The spinal corrective device 110 is formed at least partially or entirely of a shape memory material, which may be a shape memory polymer or alloy, such as nitinol (a nickel-titanium alloy), to create corrective forces that are applied to the spinal column. In the austenitic phase, the spinal rod 110 has a pre-selected shape matching a corrected or desired shape of the spine. In the martensitic phase, the spinal rod 110 is flexible and malleable to match the shape of the spine in the deformed shape. The spinal corrective device is attached to the connectors or bone anchors while in the martensitic state, and subsequently returned to the austenitic state while attached to the connectors or bone anchors to apply corrective forces to the spine and return the spine to a corrected or desired shape.

The spinal corrective element may have a circular cross-section, a polygonal-shaped cross-section or a cross-section with any other suitable shape. For the illustrative spinal rod 110 preferably has square cross-section to provide torsional correction and stability during correction of the spinal defect.

While the illustrative system comprises a single spinal rod 110, the spinal correction system 10 may alternatively comprise two spinal rods 110 or other spinal corrective elements straddling the vertebrae and connected directly to the bone anchors 120A and 120B or via intermediate connectors 152 and bridges 150.

In the illustrative embodiment of the invention the shape memory material in a spinal corrective device used for correcting a spinal defect transitions between martensitic and austenitic states by changing the temperature of the material. The spinal corrective device may be cooled to make the material flexible in a martensite state, and subsequently heated to return the material to the original shape with the austenitic structure. For example, in one embodiment, a material in the martensitic state returns to the pre-selected shape of the austenitic state by changing the temperature of the material, usually by heating the material, above a an austenite start temperature, and preferably past the austenite finish temperature. The shape memory material can transition to the martensitic state to allow deformation and shaping of the spinal corrective device by changing the temperature of the material (i.e., cooling the material) below the martensite start temperature and preferably below the martensite finish temperature.

The invention provides improved devices and methods for transfer heat from a spinal corrective device, such as the spinal rods 110, to cool a shape memory material in the spinal corrective device to transition the material to or maintain the material in a martensitic state to allow shaping and manipulation of the spinal correction device during a spinal corrective surgery. The system and method for cooling may comprise applying a coolant, such as cold gas, directly or indirectly to the material to transfer heat away from the material to induce the transition to a martensitic state. The cooling can be applied in-vivo, while the spinal corrective element is implanted in the patient's body, or external to the patient's body. In addition, the cooling can be applied along segments of the spinal corrective device, or evenly along the entire device.

A temperature sensor and/or a feedback mechanism may be provided to allow for control of the heating and/or cooling and/or other transition-inducing parameter. For example, a sensor may measure the temperature of the shape memory material in the spinal corrective element, which may be used to adjust the heating and/or cooling of the material to control the transition between the martensitic and austenitic states.

Figure 2:
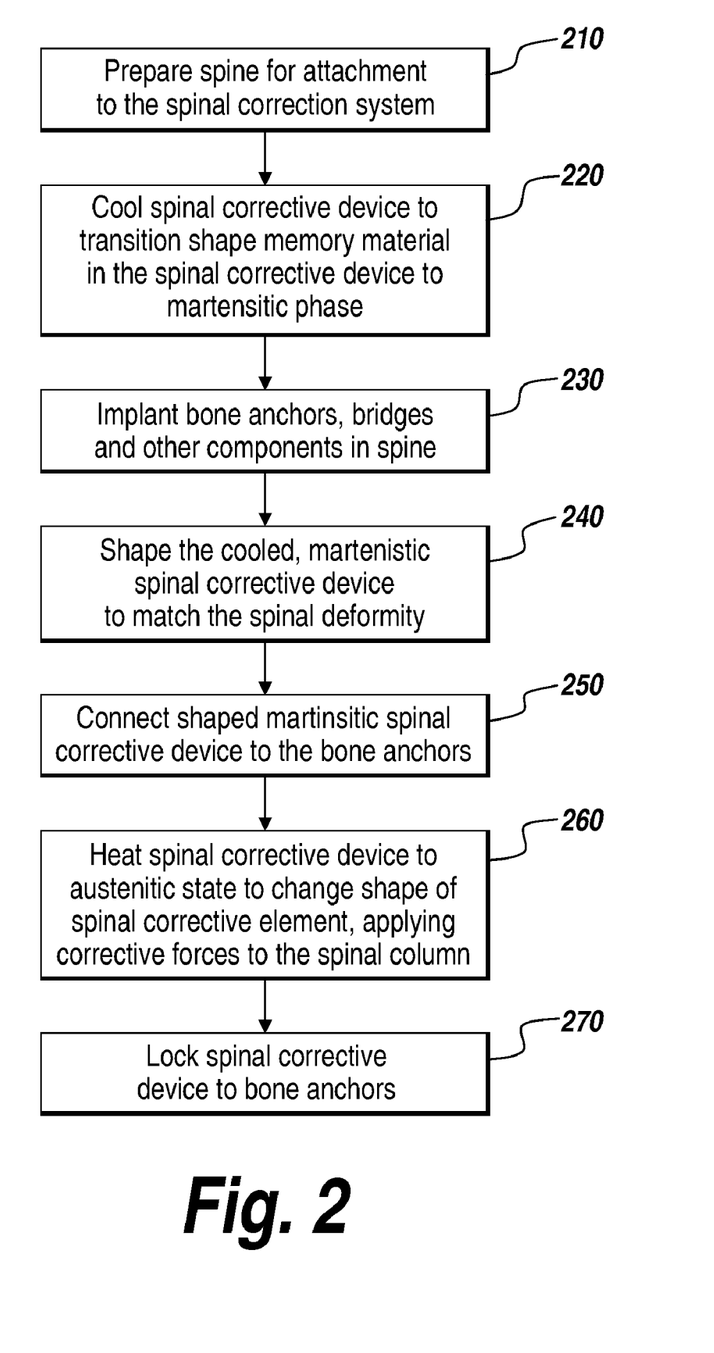
FIG. 2 illustrates the steps involved in performing a spinal corrective surgery according to an illustrative embodiment of the invention.

FIG. 2 illustrates the steps involved in performing a spinal corrective surgery using a spinal correction system according to an embodiment of the invention. In step 210, the spine is prepared for attachment to the spinal correction system by opening the patient to expose the spine. In step 220, one or more spinal corrective devices, such as a spinal rod 110, formed at least partially of a shape memory material, such as nitinol, are cooled to transition the spinal corrective device to a martensitic phase, making the device malleable and deformable. The device is preferably cooled below the martensite final temperature of the material, to provide sufficient time to manipulate the spinal corrective device in the martensite state, while being maintained above a certain temperature to avoid cold burns to the patient. For a nitinol material, the transition from martensitic to austenitic state and vice versa is characterized by a martensite start temperature of between about 10 and about 15 degrees Celsius, a martensite final temperature between about 10 and about 20 degrees Celsius below the martensite start temperature, an austenite start temperature of between about 0 and about 10 degrees Celsius and an austenite final temperature of about 32 degrees Celsius. For a nitinol spinal rod, the rod is preferably cooled from a temperature of about 25 degrees Celsius to a temperature of between about −20 and about −30 degrees Celsius to transition the material to the martensitic state, though one skilled in the art will recognize that the temperature to which the device is cooled may vary.

The spinal corrective device may be provided initially in the austenitic state, where the device has the shape of an expected corrected spine. The initial spinal corrective element may have any of a variety of lengths and curvatures to accommodate particular anatomical variations of the individual patient.

After cooling in step 220, the spinal corrective device 110 may be stored in ice-water or another cold environment to maintain the material in the martensite state.

As described in detail below, the spinal corrective device may be cooled in step 220 through a variety of means. For example, the spinal corrective device 110 may be cooled by applying a cold gas or other coolant directly or indirectly to the spinal corrective device.

In step 230, the bone anchors 120, such as polyaxial screws, and bridges 150 are implanted in the spine at selected locations for receiving the spinal corrective device 110. Alternatively, the bone anchors and bridges are implanted before the cooling of the spinal corrective device in step 220.

After the bone anchors 120 are implanted and the spinal corrective device 110 is transitioned to the martensitic state, the cooled, martensitic spinal corrective device 110 is shaped to match the spinal deformity in step 240. The spinal corrective element may be shaped manually, using benders, or using any suitable instrument. Shaping the flexible spinal corrective device to match the deformity allows the spinal corrective element to match and fit into receiving portions on the bone anchors or other components already connected to the spine.

In one embodiment, a phantom spinal rod may be used in step 240 to shape a martensitic spinal rod to match a spinal deformity. The phantom spinal rod is flexible and may be bent and/or twisted to fit into the receiving-portions to determine the shape of the deformed spine. The cooled spinal corrective device 110, which is flexible and deformable while below the martensite start temperature, and is preferably below the martensite finish temperature, is bent and/or twisted to match the phantom spinal rod, and thus the spinal deformity.

In step 250, the shaped spinal corrective device is placed in receiving portions of the bone anchors 120, and secured thereto. Approximators may be used, if needed, to approximate the spinal corrective device into the receiving portions. During step 250, the temperature of the spinal corrective device is preferably maintained at a sufficiently low temperature, below the austenite start temperature to prevent transition back to the austenite state, allowing the surgeon bend, handle and place the spinal corrective device in the patient. The shaped martensitic spinal corrective device is then fixed to the bone anchors, either directly or indirectly, to be able to withstand a selected amount of corrective force for correcting the spinal deformity.

In step 260, the spinal corrective device is transitioned to the austenitic state, which returns the spinal corrective device to the pre-selected shape of the expected corrected spine to apply corrective forces to the spinal column. In the illustrative embodiment, the spinal corrective device is heated to transition the material to the austenitic state. Preferably, the surgeon transitions the spinal corrective device to the austenitic state by heating the spinal corrective element to or past the austenitic start temperature, and preferably past the austenite finish temperature. The corrective forces in the spinal corrective device 110 are transferred through the bone anchors 120 to the spine. Due to its visco-elastic properties, the deformed spine with be corrected by the corrective forces of the system.

Any suitable means may be used to transition the spinal corrective device to the austenitic state. For example, a heater for heating a shape memory material in a spinal corrective device may employ a heated liquid that circulates near or in contact with the shape memory material to raise the temperature of the shape memory material into the austenitic state. Alternatively, a heater may employ induction heating, resistance heating, electromagnetic radiation heating and/or any other suitable means for increasing the temperature of the shape memory material. According to one embodiment, body heat may be used to partially or fully heat the shape memory material to the austenitic state.

Preferably, the shape memory material is heated above the austenitic final temperature and above body temperature to create sufficient force to move the spine into the corrected configuration, while keeping the temperature sufficiently low (i.e., equal to or below about 40 degrees Celsius) to prevent burns to the body.

The correctional force applied to the spine to correct the spinal deformity is preferably applied evenly and spread across the vertebral bodies.

Figure 3:
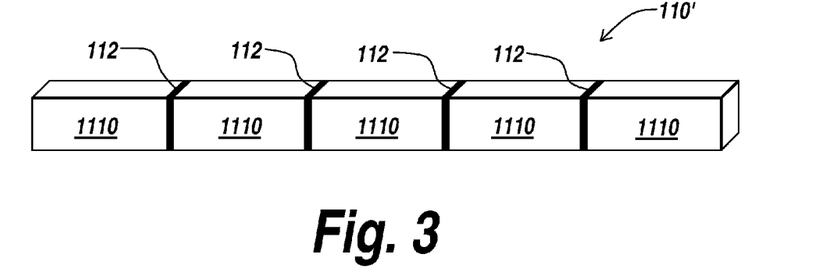
FIG. 3 illustrates an embodiment of a spinal corrective device including insulation between different segments of the device to facilitate segmental heating and/or cooling of the spinal corrective device.

In one embodiment of the invention, isolated segments of the spinal corrective device may be controllably transitioned between the martensitic state and the austenitic state at a time. For example, as shown in FIG. 3, an embodiment of the spinal corrective device 110' may have insulation 112 between different segments 1100 of the device to prevent heat or cooling from transmitting from one segment to another to facilitate segmental correction.

In another embodiment, the entire spinal corrective device may transmit heat, so that heating a portion of the spinal corrective device transmits heat to or removes heat from other portions of the spinal corrective device to transition the entire spinal corrective device to an austenitic state or a martensitic state.

According to one embodiment, the vertebrae are fully corrected during the surgical procedure, i.e., the temperature of the shape memory material increases past the austenite final temperature during the surgical procedure, so that no additional transition occurs after surgery.

According to another embodiment, the vertebrae are not fully corrected during the surgical procedure, to allow for post-operative correction as the body heat continues to heat the spinal corrective device up to body temperature after surgery, allowing for post-operative movement. In this manner the spinal defect may be reduced fully over an extended period of time.

In step 270, the spinal corrective device may be locked in the anchors using set screws or another locking mechanism.

According to one aspect of the invention, the spinal corrective device 110 may be cooled while disposed in the body to allow shaping of the corrective device while attached to the bone anchors. The in-vivo cooling of the spinal corrective device allows for control of the corrective forces applied to the spine. For example, if excessive or damaging force is applied to the spine during transition to the austenitic state in step 260, a cooling device may selectively and controllably cool the shape memory material in-vivo to remove some of the corrective force and loosen the spine. Then, heating may be subsequently controllably applied to the shape memory material to reapply the corrective forces to the spine. Alternatively, after releasing the spine by in-vivo cooling, additional anchoring devices may be inserted and connected to the spinal corrective device to spread the load of the corrective forces over a greater area to reduce damage.

A variety of different devices and methods may be used to cool the shape memory material of a spinal corrective device to a martensitic state in step 220 or after attachment to the spine to allow shaping of the spinal corrective device. For example, in one aspect, a coolant circulating through a cooling device creates a cooling effect by drawing heat out of the opposing material until the temperatures of the coolant and material reach a balance, or the cooling device is removed. Examples of suitable coolants include, but are not limited to, water, a salt solution, which freezes at a lower temperature than water, and liquid gases, such as carbon dioxide, nitrous oxide, nitrogen, a mixture of butane, propane and mixer, and other gases suitable for removing heat by the vaporization of the gas on a spinal corrective device.

Figure 4:
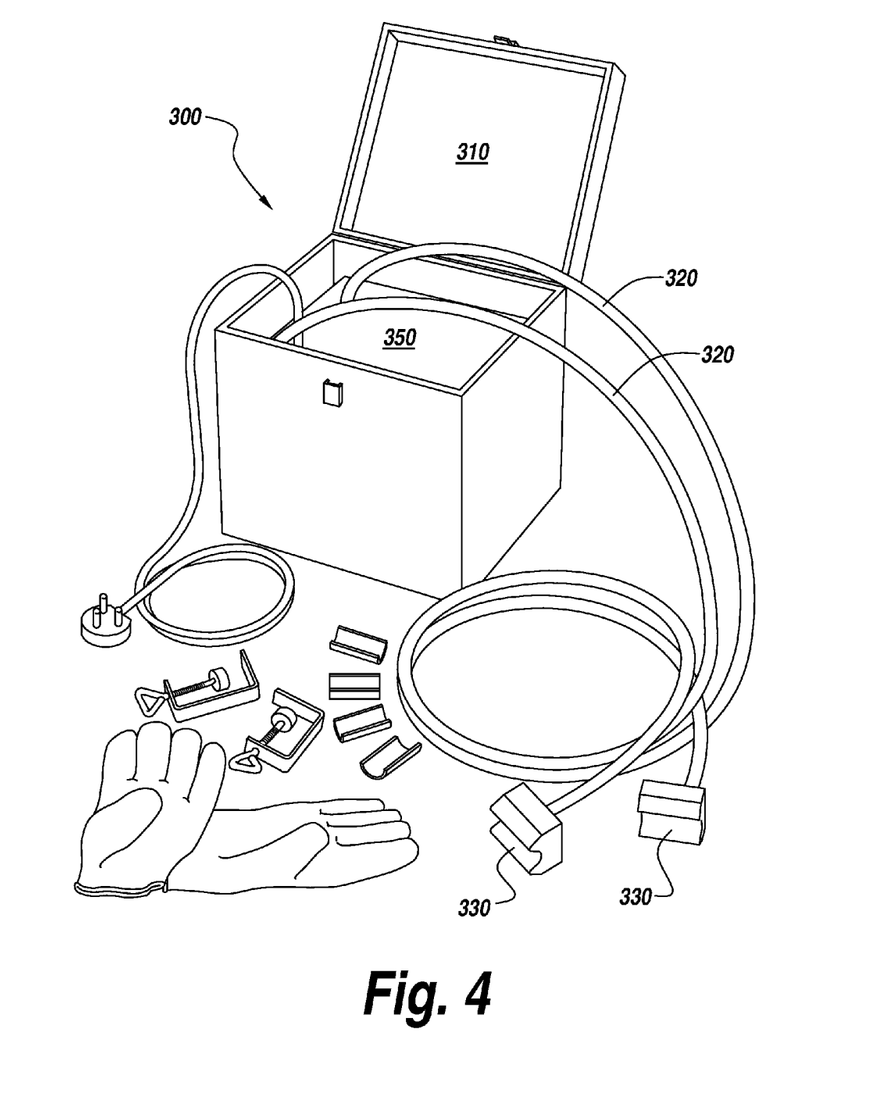
FIG. 4 illustrates a cooling device for a spinal corrective device according to one embodiment of the invention.

The cooling device for applying a cold liquid to cool a spinal corrective device can have any suitable size, shape, configuration and cooling means. For example, as shown in FIG. 4, a cooling device 300 of one embodiment of the invention may be a hand held device, similar to pipe freezing equipment used to form a plug of ice in a pipe. As shown suitable cooling device according to one embodiment of the invention may include one or more refrigeration units 310 that circulate self-contained refrigerant from a source 350 via fluid paths 320 to freeze heads 330, which are preferably formed of aluminum or another suitable heat-transmitting material. The freeze heads couple to or are brought into proximity with the spinal corrective device to cool the shape memory material in the spinal corrective device. The freeze heads 330 may be configured to fit over the spinal corrective element, to allow cooling both externally and in-vivo. Examples of suitable equipment include, but are not limited to, the "Super-Freeze Pipe Freezing Unit" from RIDGID® Tool, a subsidiary of Emerson of St. Louis, Mo., the Freeze Master 280D and/or 350D, available from B.E.S. Ltd. Of Birmingham, UK, and other similar products.

Figure 5:
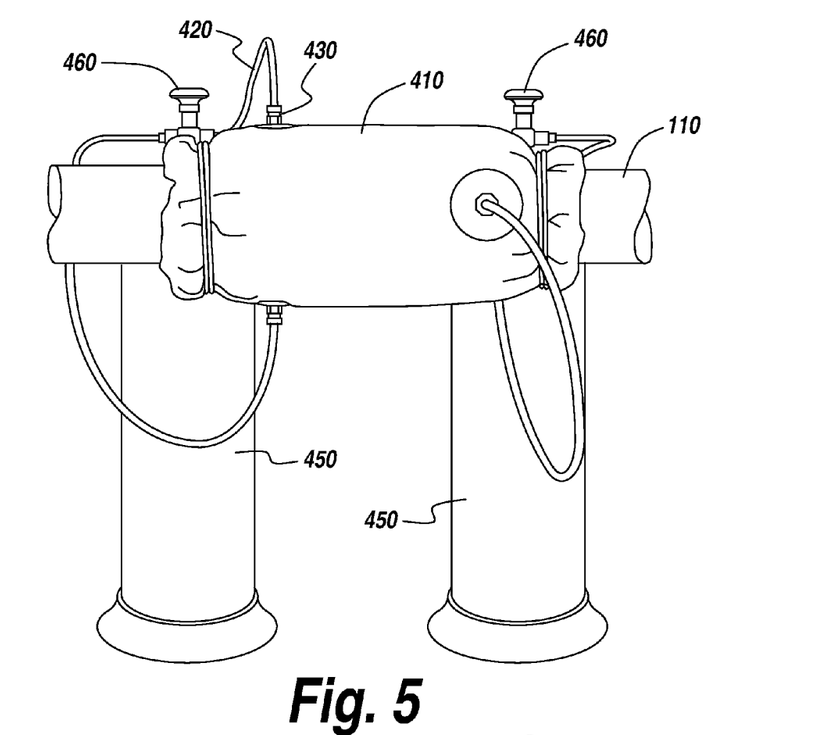
FIG. 5 illustrates another embodiment of a cooling device for a spinal corrective device according to another embodiment of the invention.

The cooling device for cooling a spinal corrective device 400 may alternatively comprise a jacket 410 or collar that circulates coolant from a coolant source 450, as shown in FIG. 5. The jacket may be wrapped around the location on the spinal corrective device 110 where the cooling is required or along the entire length of the spinal corrective device. A nozzle 430 on the jacket is coupled to a source of liquid gas 450, such as a cylinder of liquid carbon dioxide ($CO_2$) or liquid nitrogen ($N_2$), by means of a high pressure hose 420 or other suitable fluid path. Valves 460 or other flow controllers may be used to control the flow of cooling gas through the fluid paths and jacket 410 When liquid gas is injected into the space between the jacket and spinal corrective device, the gas expands to form a solid plug at a low temperature. For example, liquid carbon dioxide expands to form dry ice at a temperature of −109 degF. The jacket 410 is preferably insulated. The low temperature quickly cools the shape memory material in the associated spinal corrective device. Examples of suitable cooling jackets forming the cooling device according to one embodiment of the invention include, but are not limited to the "Qwik Freezer" portable pipe freezing equipment available from Cob Industries, Inc., of Melbourne, Fla., CRYO-LATER™ Pipe Freeze Seal Products from Cryostop International, Inc., of Wilmington, N.C., the Accu-Freeze, which utilizes liquid nitrogen in a controlled system to freeze a selected section of a device, available from Cob Industries, Inc., and other similar products.

The Accu-Freeze product, which may be used in accordance with the teachings of the invention, comprises an insulated jacket, copper tubing that is wrapped around the section of the device to be cooled, and a liquid nitrogen source. The nitrogen is injected through a control system, which controls the flow of the liquid nitrogen through the insulated jacket based on the temperature of the opposing device being cooled. The liquid nitrogen cools the section of the device wrapped by the jacket, which may be the entire length of the spinal correction device, or one or more selected sections.

The jacket 410 may also selectively circulate a heating fluid to heat the shape memory material to an austenitic state.

Figure 6:
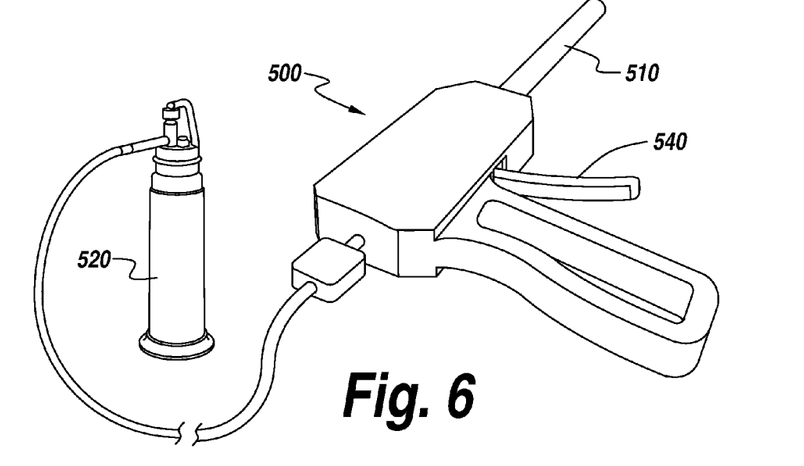
FIG. 6 illustrates a cooling device including a cooling tip for cooling a spinal corrective device according to another embodiment of the invention.

Alternatively, the cooling device 500 for cooling a spinal corrective device may have a tip 510 through which a coolant from a coolant source 520, such as cold gas, including, but not limited to nitrogen and carbon dioxide, circulates to create a cold spot, as shown in FIG. 6. The cold tip 520 contacts or is brought into close proximity with the corrective device to cool the corrective device. The illustrative device 500 further includes a trigger 540 for controlling circulation of coolant to the tip 520, and a handle 570 to allow a user to easily grasp and direct the cooling device. An example of such a device is the ERBE cooling gun from BAAT Medical Engineering or the ERBOKRYO 12 (also called the "Cryo Gun"), available from ERBE Elektromedizin of Tübingen, Germany. The ERBE cooling gun is also capable of spraying a cold liquid gas directly on a location of the spinal corrective element to cool the shape memory material to a martensitic state.

The cooling devices 300, 400 and 500 of FIGS. 4-6 are preferably sealed systems, allowing reuse of the cooling device for several cooling processes, without requiring refilling of the devices. The cooling devices 300, 400 and 500 also facilitate control over the location of the cooling process.

Figure 7:
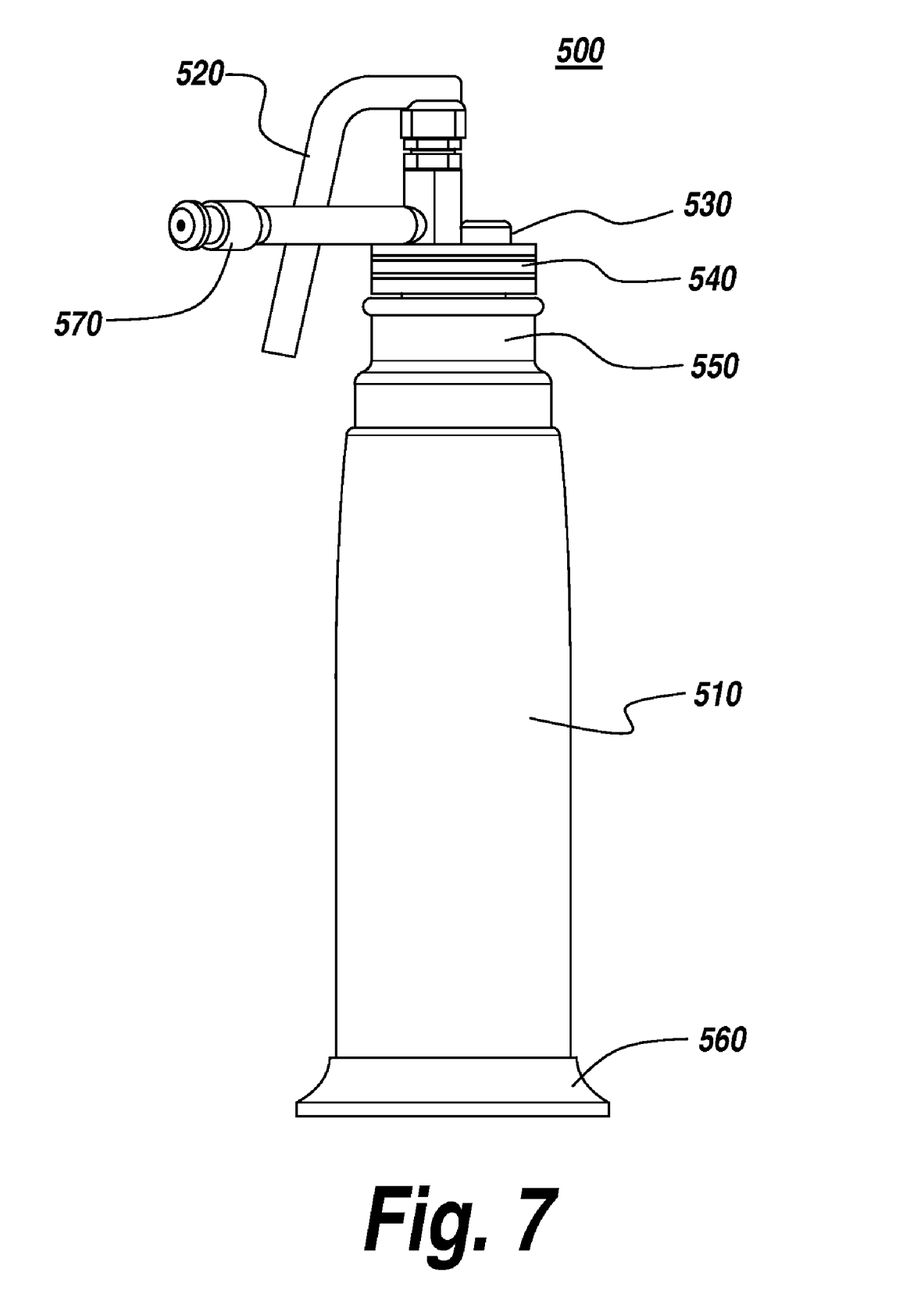
FIG. 7 illustrates a cooling device comprising a canister of compressed cooling gas in another embodiment of the invention.

In another embodiment, a shown in FIG. 7, a coolant, which may be a gas, such as carbon dioxide, nitrous oxide and nitrogen, may be sprayed from a pressurized source 500 directly on a spinal corrective device to cool the shape memory material in the spinal corrective device. As the coolant is released from the source, the coolant expands, creating a cooling effect that causes very rapid and predictable cooling of the shape memory material. The gas in the coolant vaporizes almost instantly once released from a canister or other pressurized source, drawing heat away from anything it comes into contact with (i.e., the spinal corrective device), drawing heat away from the spinal correction device.

In the illustrative embodiment, the cooling device 500 include a pressurized source includes a pressurized chamber 510 for holding the liquid gas, a trigger 520 for releasing the liquid gas and a relief valve 530 for maintaining a substantially constant operating pressure of the cooling gas. A vent 540 may also be included to allow the internal pressure in the pressurized chamber to gradually vent to increase safety. A collar 550 may be provided to insulate the user's hand. A base 560 may provide stability of the pressurized source 500. Spray tips 570 may also be provided for directing the released gas to a selected location. A variety of spray tips of varying sized apertures may be included in the cooling system 500.

Examples of suitable canisters that may be used to spray a gas onto a spinal corrective device include, but are not limited to the CRY-AC® and CRY-AC®-3 thermal insulated canisters produced by Brymill Cryogenic Systems of Ellington, Conn. The thermal insulated canisters may hold a variety of liquid gasses and allow direct and precise release onto targeted location.

Other examples of suitable canister cooling devices for cooling a spinal corrective device during spinal corrective surgery include the Veruca-Freez™ freezing system, which is a pre-loaded canister of freezing gas, usually liquid nitrogen, available from CryoSurgery, Inc., of Nashville, Tenn., the Histofreezer® cryosurgery kit, available from OraSure Technologies, Inc., of Bethleham, Pa., Freeze 75 cooling product from CRC Industries Sweden AB of Sweden, FREEZ-IT® freeze spray available from ITW Chemitronics® of Kennesaw, Ga., which is a pre-loaded canister of freezing gas made from a mixture of butane, propane and mixer to make the gas non-combustible, medical gases available from The BOC Group of Murray Hill, N.J., which provides compressed medical gas, such as nitrous oxide, in large canisters with a thermally insulated extension tube allowing gas to be pumped to a point of need.

Other examples of suitable sources of cooling gas include cryosurgery systems, such as the Welch Allyn Cryosurgery System from Welch Allyn Medical Products of Skaneateles Falls, N.Y., as well as the Wallach WA 1000B Cryosurgery System and the Wallach LL-100 Cryosurgical system, both available from Wallach Surgical Devices, Inc., of Orange, Conn.

The cooling devices of FIGS. 4-7 allow for targeted cooling of isolated sections of a spinal corrective device, if desired. The illustrative cooling devices facilitate targeted application of the cooling gas to selected locations of the spinal corrective element to transition only at portion or selected portions of the spinal corrective device to the martensitic state. Alternatively, the cooling devices may fully cool the entire spinal corrective device.

According to another embodiment of the invention, the source of application of a cold gas to the spinal corrective device may employ a container placed on a side table in the surgery room that utilizes a thermally insulated extension tube allowing the cold gas to be pumped to the point of need.

Figure 8:
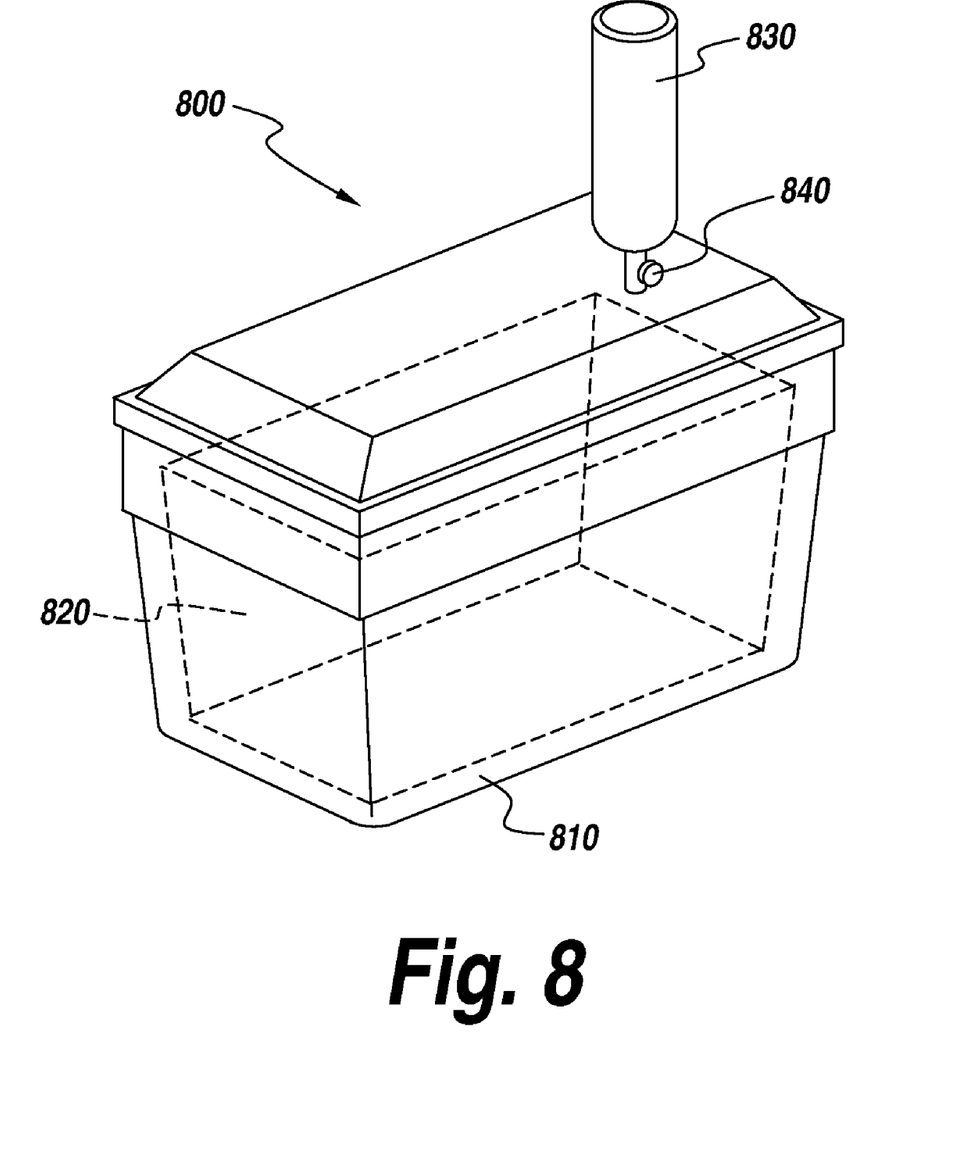
FIG. 8 illustrates a cooling device comprising an insulated chamber for cooling a spinal corrective device according to another embodiment of the invention.

In another embodiment of the invention, a cooling device for a spinal corrective element may comprise an insulated container having a source of coolant, such as a gas or a cold liquid, as shown in FIG. 8. The insulated container 800 comprises a housing 810 defining an insulated chamber 820. The insulated chamber 820 is selectively in fluid communication with a source of cold gas 830 or other coolant via a valve 840. To cool a spinal corrective device using the insulated container 800, the spinal corrective device 110 is inserted into the chamber 820 and coolant, such as cold gas, is injected from the source 830 into the chamber 820 to cool the chamber and spinal corrective device stored therein.

Other suitable cooling devices for cooling a shape memory material in a spinal corrective device include, but are not limited to: a container with liquid nitrogen or other liquid coolant, a metal cooling plate, use of Peltier elements and other cooling concepts.

The cooling device may include a thermocouple or other suitable temperature sensor for monitoring the temperature of the spinal corrective device during cooling. The cooling process may be controlled based on feedback from the temperature sensor.

The cooling devices and method of cooling provide significant advantages over prior methods for cooling spinal corrective devices, including enhanced control over the cooling process, the ability to provide segmental transition to the martensitic state, in-vivo cooling of the spinal corrective element to enhance control over the corrective forces applied to the spine, more thorough cooling of the spinal corrective element and other advantages.

The present invention has been described relative to an illustrative embodiment and application in spinal correction surgery. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A method of cooling a spinal correction device comprising a shape memory material, comprising the steps of:
    inserting in a body of a patient a spinal correction device comprised at least partially of a shape memory material;
    applying a cold gas to the spinal correction device when implanted in the body of the patient to transition at least a portion of the shape memory material from an austenitic state to a martensitic state;
    sensing a temperature of the shape memory material of the spinal correction device where the cold gas is applied; and
    adjusting the applying the cold gas to the spinal correction device based on the sensed temperature of the shape memory material;
    adjusting a shape of the spinal correction device transitioned to the martensitic state to match a spinal deformity of the patient;
    inserting the shaped spinal correction device in receiving portions fixed to vertebrae of the patient; and
    heating the spinal correction device inserted in the receiving portions to transition the spinal correction device from the martensitic state into the austenitic state and to apply corrective forces to the vertebrae of the patient, wherein the spinal correction device has a corrected shape of the vertebrae in the austenitic state.

2. The method of claim 1, wherein the cold gas comprises one of liquid nitrogen, carbon dioxide and nitrous oxide.

3. The method of claim 1, wherein the step of applying the cold gas comprises inserting the spinal correction device in an insulated device having a compartment, and injecting the cold gas into the compartment.

4. The method of claim 1, wherein the step of applying the cold gas to the spinal correction device comprises circulating the cold gas through a jacket coupled to the spinal correction device.

5. The method of claim 1, wherein the step of applying the cold gas comprises releasing gas from a pressurized canister.

6. The method of claim 1, wherein the cold gas is applied to a portion of the spinal correction device.

7. The method of claim 1, wherein the cold gas is applied along the length of the spinal correction device.

8. The method of claim 1, further comprising the step of adjusting the shape of the spinal correction device while in the body.

9. The method of claim 1, wherein the cold gas is applied directly to the spinal correction device and then evaporates.

10. The method of claim 1, wherein the cold gas is circulated through a system to draw heat away from the spinal correction device.

11. The method of claim 10, wherein the system also selectively transfers heat to the spinal correction device to heat the shape memory material to an austenitic state.

12. The method of claim 1, wherein the shape memory material comprises a shape memory metal.

13. The method of claim 1, wherein the shape memory material comprises nitinol.

14. A method of correcting a spinal deformity, comprising the steps of:
implanting a spinal correction device in a body of a patient, wherein the spinal correction device includes a spinal rod having a square cross-section to provide torsional correction and stability during correction of the spinal deformity, the spinal rod includes a first portion and a second portion each formed of a shape memory material, and the first portion and the second portion are insulated by an insulation portion; and
cooling the spinal correction device after implantation in the body to maintain the shape memory material in a martensitic state, wherein the step of cooling comprises cooling the first portion of the spinal correction device separately from the second portion of the spinal correction device so that the first portion is transitioned from an austenitic state to the martensitic state while the second portion remains in the austenitic state.

15. The method of claim 14, further comprising the step of adjusting the shape of the spinal correction device while in the body.

16. The method of claim 14, wherein the step of cooling comprises applying a cold gas to the spinal correction device.

17. The method of claim 16, wherein the cold gas is directly applied to the shape memory material.

18. The method of claim 16, wherein the cold gas is circulated through a fluid path adjacent to the spinal corrective device to draw heat from the shape memory material.

19. A method of cooling a spinal correction device comprising a shape memory alloy, comprising the steps of:
implanting and isolating a first shape memory portion from a second shape memory portion in a spinal correction device by including an insulation portion between the first shape memory portion and the second shape memory portion, each of the first shape memory portion and the second shape memory portion including a shape memory alloy, wherein the spinal correction device includes a spinal rod having a square cross-section to provide torsional correction and stability during correction of a spinal deformity;
cooling the first shape memory portion of the implanted and isolated spinal correction device without affecting the temperature of the second shape memory portion of the spinal correction device so that the first shape memory portion is transitioned from an austenitic state to a martensitic state while the second shape memory portion remains in an austenitic state; and
heating the spinal correction device to transition from the martensitic state into the austenitic state to apply corrective forces to the spine, wherein the spinal correction device has a shape of a corrected spine in the austenitic state.

20. The method of claim 19, wherein the step of cooling the portion of the spinal corrective device comprises applying a cold gas to the segment.

21. The method of claim 20, wherein the cold gas comprises one of liquid nitrogen, carbon dioxide and nitrous oxide.

22. The method of claim 19, wherein the step of cooling a portion of the spinal correction device comprises circulating a coolant through a jacket coupled to the portion of the spinal correction device.

23. The method of claim 19, wherein the step of cooling a portion of the spinal correction device comprises releasing a pressurized cooling gas from a pressurized canister and directing the released gas to the segment.

* * * * *